(12) United States Patent
Hansen

(10) Patent No.: US 12,721,757 B2
(45) Date of Patent: Sep. 1, 2026

(54) METHOD FOR PROCESSING NONWOVEN SHEETS BY COMBINED ACTIVATION AND BONDING

(71) Applicant: FIBERTEX PERSONAL CARE A/S, Aalborg Ost (DK)

(72) Inventor: Morten Rise Hansen, Aalborg (DK)

(73) Assignee: FIBERTEX PERSONAL CARE A/S, Aalborg Ost (DK)

( * ) Notice: Subject to any disclaimer, the term of this patent is extended or adjusted under 35 U.S.C. 154(b) by 440 days.

(21) Appl. No.: 18/284,873

(22) PCT Filed: Nov. 10, 2021

(86) PCT No.: PCT/EP2021/081233
§ 371 (c)(1),
(2) Date: Sep. 29, 2023

(87) PCT Pub. No.: WO2022/242891
PCT Pub. Date: Nov. 24, 2022

(65) Prior Publication Data
US 2024/0189156 A1 Jun. 13, 2024

(30) Foreign Application Priority Data
May 17, 2021 (EP) .................................... 21174142

(51) Int. Cl.
*A61F 13/15* (2006.01)
*A61F 13/49* (2006.01)

(52) U.S. Cl.
CPC .. *A61F 13/15699* (2013.01); *A61F 13/15731* (2013.01); *A61F 13/15764* (2013.01);
(Continued)

(58) Field of Classification Search
CPC ......... A61F 13/15699; A61F 13/15731; B32B 3/30; B32B 5/002; B32B 7/05
See application file for complete search history.

(56) References Cited

U.S. PATENT DOCUMENTS

2006/0003656 A1 1/2006 Morman
2009/0035527 A1* 2/2009 Kobayashi ............ D04H 1/593 428/167

(Continued)

FOREIGN PATENT DOCUMENTS

CN 101848807 A 9/2010
CN 109803818 A 5/2019

(Continued)

OTHER PUBLICATIONS

Office Action issued in corresponding Chinese Patent Application No. 202180096852.3 issued Jan. 27, 2026 (18 pages).

(Continued)

*Primary Examiner* — Daniel Mcnally
(74) *Attorney, Agent, or Firm* — Kilyk & Bowersox, P.L.L.C.

(57) ABSTRACT

The invention relates to a method for manufacturing nonwoven sheets that includes a step of combined activation and bonding. The invention further relates to an application of this method to the making of elastically stretchable nonwoven laminate sheets, sheets produced by such method, and to uses for such sheets.

11 Claims, 6 Drawing Sheets

Figure 1:
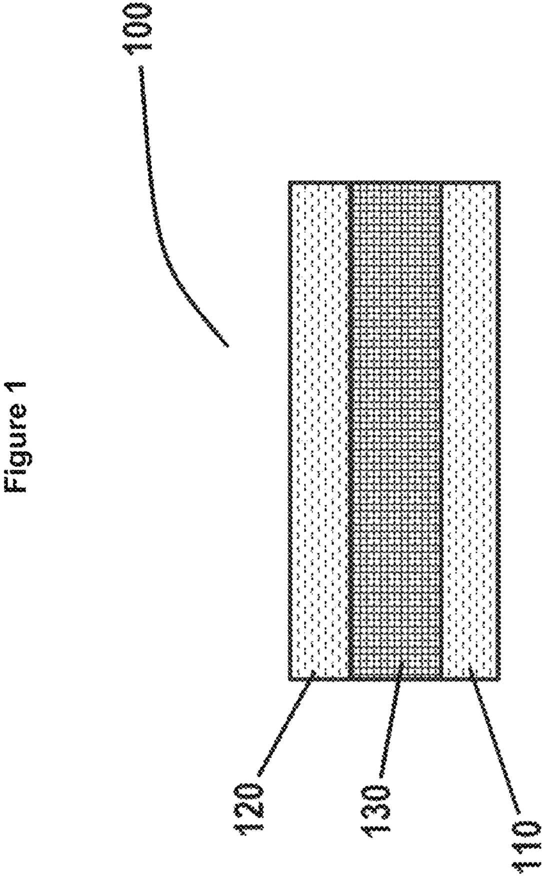

(52) U.S. Cl.
CPC ............... *A61F 2013/15861* (2013.01); *A61F 2013/49023* (2013.01)

(56) References Cited

U.S. PATENT DOCUMENTS

| | | | |
|---|---|---|---|
| 2009/0068420 A1 | 3/2009 | Pascavage | |
| 2012/0078209 A1* | 3/2012 | Sakai | A61F 13/53 604/378 |
| 2018/0099483 A1 | 4/2018 | Jackson | |
| 2019/0309458 A1 | 10/2019 | Ellingson et al. | |
| 2020/0307146 A1 | 10/2020 | Wagner et al. | |
| 2021/0388548 A1 | 12/2021 | Takaku et al. | |

FOREIGN PATENT DOCUMENTS

| | | |
|---|---|---|
| EP | 3426214 A | 1/2019 |
| JP | 2007191829 A | 8/2007 |
| KR | 10-20080018259 A | 2/2008 |
| KR | 10-1405888 B1 | 6/2014 |
| KR | 10-20190039030 A | 4/2019 |
| WO | 2007001270 A1 | 1/2007 |
| WO | 2017061165 A1 | 4/2017 |
| WO | 2020085502 A1 | 4/2020 |
| WO | 2020187540 A1 | 9/2020 |

OTHER PUBLICATIONS

Office Action issued in corresponding Korean Patent Application No. 10-2023-7033562 issued Jan. 19, 2024 (with English translation) (11 pages).

International Search Report and Written Opinion issued in corresponding International Patent Application No. PCT/EP2021/081233 mailed Feb. 18, 2022 (9 pages).

Third Party Submission of Publications submitted in corresponding Japanese Patent Application No. 2023-560186 on Nov. 29, 2024 (4 pages).

Office Action issued in corresponding Indian Patent Application 202317064069 dated Apr. 21, 2026 (9 pages).

* cited by examiner

METHOD FOR PROCESSING NONWOVEN SHEETS BY COMBINED ACTIVATION AND BONDING

This application is a National Stage Application of PCT/EP2021/081233, filed Nov. 10, 2021, which claims priority to European Patent Application No. 21174142.6, filed May 17, 2021.

The invention relates to a method for making nonwoven sheets that includes a step of combined activation and bonding. The invention further relates to an application of this method to the making elastically stretchable nonwoven sheets, sheets produced by such method, and to uses for such sheets.

Nonwoven sheets are used in the hygiene industry as materials for making baby diapers and similar products on a large scale. In many instances, for example to make back-ears in open diapers or waist belt portions in pant-like baby diapers, however, elastically stretchable materials are required and standard nonwoven sheets do not meet that requirement.

Traditional approaches to address the problem of a limited elastic stretch of the nonwoven sheets comprise including an elastic film between layers of nonwoven material. The resulting laminates can have good elastic performance, but elastic films are not air permeable and this can lead to discomfort to the wearer. Another approach comprises including elastic strands, typically referred to as Lycra strands, into the sheets. The drawback of this method is a localized elastic force that may also lead to discomfort to the wearer, and a proneness of the strands to break during production.

Additionally, the incorporation of an elastic film or strand renders the sheets elastic, but only within the boundaries of the maximum stretch of the nonwoven materials associated with the elastic film or strand. Most traditional nonwoven materials have elongation at break values of around 50-80% in machine-direction (MD) and 70-100% in cross-machine direction (CD) (WSP 110.4) maximum, and most usually even less, meaning that they only elongate to a very limited extent before they are destroyed. For the applications specified above, however, the sheets would be required to elastically stretch for 150% of their original dimension (to 250% of their original dimension) and, depending on the specific application, this requirement can apply to cross-machine directional or machine directional stretch. For example, for making a traditional open or taped baby diaper, typical production processes require the material used for a back ear laminate to exhibit an elastic stretch in that magnitude in CD. For making adult or baby diaper pants, on the other hand, typical production processes require the material used for elastic applications therein, like belts, to exhibit an elastic stretch in that magnitude in MD.

The traditional approach to address the problem of limited stretch of the nonwoven materials within the laminate sheets is pleating the nonwoven materials upon lamination to the elastic film or strand. This way, the lack of extensibility of the nonwoven material itself is compensated by storing additional material in each pleat. The disadvantage of pleating, however, is the need for more material during production and the higher thickness of the final product, which is negatively perceived by the customer due to increased thermal insulation and more visible appearance.

Nonwoven sheets, which have an inherent ability to elastically stretch, are disclosed in WO 2020/187540 A1. The respective sheets comprise an elastic spunbonded web formed from elastic fibers and spunbonded carrier nonwovens formed from crimped fibers, and are pre-stretched by passing them through an activation unit comprising a pair of interacting corrugated rollers. While the elastic web can go without bonding, a bonding of the carrier layers is necessary to provide a useful nonwoven material. At the same time, the necessary bonding of the carrier layers significantly limits the extent to which these layers can be pre-stretched without destroying them, because the bonding locks the fibers in position and limits the potential for rearrangement. An open dot bonding pattern and the use of crimped fibers makes the carrier layers more flexible than traditional nonwoven fabrics, such that an elastic stretch to about 250% of their original dimension can be obtained at least in CD, insofar meeting the industry requirements, but elastic stretch in MD is more limited for these sheets.

An alternative approach to making nonwoven sheets having an inherent ability to elastically stretch is disclosed in EP 3 715 517 A1. The method disclosed in this reference relies on an in-line process and bonding together of carrier layers and elastic layers before activating the sheet in an already bonded state. Despite the use of crimped fibers also in this fabric, the bonded nature of the carrier layers before activation limits the extent to which the sheet can be pre-stretched without destroying it.

There is hence a need in the hygiene industry for nonwoven sheets which have an even higher inherent ability to elastically stretch, especially in machine direction but also in cross-machine direction.

In an attempt to solve this problem, a concept was developed herein that not only solves this problem, but is also more generally applicable to nonwoven processing in other respects.

Specifically, the invention suggests a method for manufacturing a nonwoven sheet. The method comprises a step (a) of providing a precursor sheet. Further, the method comprises a step (b) of concurrently activating and bonding the precursor sheet to obtain the nonwoven sheet, wherein the activating comprises passing the precursor sheet between a pair of activation rollers having a plurality of meshing ribs and grooves arranged in parallel on their collaborating surfaces, thereby stretching the precursor sheet in a direction perpendicular to the orientation of the ribs and grooves, and wherein the bonding comprises an embossing of bonding points into the precursor sheet while it is stretched, the embossing being effected by embossing projections that are arranged along the crests of the ribs and/or grooves on the activation roller surfaces.

In one embodiment, the ribs and grooves are oriented in machine direction and extend annularly over the surfaces of the rollers, such that the precursor sheet is stretched in cross-machine direction.

In another embodiment, the ribs and grooves are oriented in cross-machine direction and extend axially over the surfaces of the rollers, such that the precursor sheet is stretched in machine direction.

The precursor sheet may be a bonded nonwoven material having one or more layers. In a preferred embodiment, it may be a calender-bonded material.

Alternatively, the precursor sheet may be an unbonded fibrous web. Such webs are consolidated fibers and are unbonded precursors to the nonwoven materials. Since the fibers forming for the webs are not bonded by calender embossing and preferably also not bonded by other bonding processes like needling or spunlacing, they are still quite mobile and have a much higher potential for rearrangement within the web than fibers of bonded layers, like in the sheets of WO 2020/187540 A1. Therefore, it may be possible to apply a more significant pre-stretching, of beyond 150% can be realized in both MD or CD, as needed, without destroying the structure, when compared to already bonded precursor materials.

Most preferably, the nonwoven material or fibrous web comprises at least one spunbond layer. Examples comprise single layer S materials, multi-layered Sn materials, or SM- or SMS-type layered fabrics that combine spunbonded layers with melt-blown layers.

In a preferred embodiment, the method is a method for manufacturing an elastically stretchable nonwoven sheet, the sheet comprising a first nonwoven carrier layer, an elastic nonwoven layer comprising elastic fibers, and, optionally, a second nonwoven carrier layer, and the precursor sheet provided in step (a) comprises a first carrier structure, which is a precursor of the first nonwoven carrier layer of the sheet to be formed, an elastic structure comprising elastic fibers, which is a precursor of the elastic nonwoven layer of the sheet to be formed, and, optionally, a second carrier structure, which is a precursor of the optional second nonwoven carrier layer of the sheet to be formed.

In one variant of this embodiment, the first carrier structure is an unbonded fibrous carrier web, wherein the elastic structure is an unbonded elastic layer precursor web comprising elastic fibers, and wherein the optional second carrier structure is a second unbonded fibrous carrier web, wherein all fibrous webs are not bonded by calender embossing.

In this variant, the concurrent bonding of the webs while in a pre-stretched state allows fulfilling the need for bonding the webs to form a solid nonwoven material without detriment to the ability for the carrier web(s) to later stretch to the extent of the pre-stretch.

Bonding in a separate step after the sheet precursor has retracted to its original dimension by the elastic force of the elastic layer, on the other hand, would largely destroy this ability because the fibers would thereby be locked in the position they assume in the retracted state.

In an alternative variant of this embodiment, the first carrier structure is a bonded nonwoven carrier layer, wherein the elastic structure is a bonded nonwoven layer comprising elastic fibers, and wherein the optional second carrier structure is a bonded nonwoven carrier layer, wherein all nonwoven layers are bonded by calender embossing.

In this variant, relatively open bonding patterns can be used in the structures to maintain a certain mobility within the pre-bonded structures, while providing an increased stability and processability. The bonding points imparted during step (b) of concurrently activating and bonding are superimposed to the existing bonding points of the fed structures.

The pre-stretching of the precursor sheet leads to localized changes in the microscopic fiber configuration of the materials. In the embodiment described above, comprising elastic and carrier layers, the changes would mainly be in the largely inelastic carrier structure(s). Specifically, the microscopic fiber configuration changes back and forth along a regularly repeating pattern that reflects the arrangement of the ribs and grooves on the roller surfaces, meaning a pattern of parallel stripes. If the ribs and grooves are oriented in machine direction, the microscopic fiber configuration of the structures changes back and forth along a regularly repeating pattern in cross-machine direction of the fabric and is constant along machine-directional lines. If the ribs and grooves are oriented in cross-machine direction, the microscopic fiber configuration of the structures changes back and forth along a regularly repeating pattern in machine direction of the fabric and is constant along cross-machine-directional lines.

The change in microscopic fiber configuration in particular pertains to the average fiber orientation and the fiber density. The stretch is usually less significant in some areas, for example along the crest lines of the ribs and grooves, and more significant in other areas, for example adjacent the crest lines. In areas of more significant stretch, the average fiber orientation will be more strongly shifted into the direction of the stretch and the fiber density will be lower.

Since the embossing projections are arranged along the crests of the ribs or grooves, the bonding points are embossed in lines that follow stripes of the pattern along which the local fiber configuration is the same. If the ribs and grooves are oriented in machine direction, the bonding points are embossed along parallel machine-directional lines along which the local fiber configuration is the same. If the ribs and grooves are oriented in cross-machine direction, the bonding points are embossed along parallel cross-machine-directional lines along which the local fiber configuration is the same. Assuming that the stretch is least significant along the crest lines, the bonding points are embossed into stripe-shaped zones of the fabric that have, on average, the highest fiber density and, on average, the highest number of fibers orientated in lengthwise direction of the stripes.

Referring specifically to the above-described embodiment of an elastically stretchable nonwoven sheet comprising elastic layers and carrier layers, due to the retraction of the then-product sheet after the pre-stretch during concurrent activating and bonding, the microscopic fiber configuration in the stripe-shaped zones of the product sheet that are in between the lines of bonding points changes when compared to the stretched structure. Hence, in the product sheet, it is not any more necessarily true that the fiber density is highest or that an average fiber orientation is most pronounced along the lines of the bonding points. Still, also in the product sheet, the microscopic fiber configuration changes back and forth along a regularly repeating pattern of parallel stripes, and the bonding points are arranged in lines that follow stripes of the pattern along which the local fiber configuration is the same.

If a second carrier structure is present in the precursor sheet, the elastic structure is sandwiched between the two carrier structure. Likewise, in the product sheet, if a second carrier layer is present, the elastic layer is sandwiched between the two carrier layers. There can also be more than three layers by having a further elastic layer or further carrier layers or inelastic layers. Also within each layer, there may be two or more sub-layers of identical or similar kind formed by separate stages of fiber laydown in the production process.

Going back to the more general context, in one embodiment, steps (a) and (b) are subsequently carried out in line. Such an overall in-line setting can be very advantageous in terms of production efficiency.

In another embodiment, steps (a) and (b) are carried out off-line on separate lines. In one line, a precursor sheet can be provided in step (a) on one line, then rolled up and transported to another line for combined activation and bonding according to step (b) in another line. In the case of the above-described embodiment comprising elastic layers and carrier layers, the unbonded precursor sheet obtained from step (a) does not delaminate and is stable enough for handling due to inherent stickiness of the elastic fibers that are formed from a thermoplastic elastomer materials.

The extent of the (pre-)stretch of the precursor sheet during step (b), in embodiments, determines the extent to which a product fabric can be elastically stretched in a direction perpendicular to the orientation of the stripes. It may be desired that the product fabric can be elastically stretched to 150% and preferably 200% of its original dimension in the respective direction. Hence, in one embodiment, in step (b) the precursor sheet is stretched to 150% and preferably 200% of its original dimension in the direction perpendicular to the orientation of the ribs and grooves.

The stretch during activation is controlled by the distance between adjacent ribs/grooves, by how deep a rib on one roller engages in a groove on the other roller (depth of engagement), and by the width of these structures. In an exemplary embodiment, the distance between adjacent ribs/grooves can be between 1-12 mm, preferably between 3-10 mm and more preferably between 4-8 mm. The depth of engagement can be between 1-10 mm, preferably between 3-7 mm. The width of the ribs/grooves can be between 0.5-3 mm, preferably about 1 mm.

The pattern of stripes in the product sheet is such that the local fiber configuration is repeated approximately according to the sum of the distance between adjacent ribs/grooves and width of the ribs/grooves. It can hence, in one embodiment, repeat every 1-12 mm, preferably every 3-10 mm. In case one line of bonding points is embossed once per repeat, the distance between adjacent lines of bonding points is likewise 2-15 mm, preferably 5-10 mm.

Again referring specifically to the above-described embodiment of an elastically stretchable nonwoven sheet comprising elastic layers and carrier layers, the basis weight of the or each carrier precursor structure of the precursor sheet, and correspondingly carrier layer of the product sheet may be between 5-40 g/m$^2$, preferably between 8-30 g/m$^2$, more preferably between 10-25 g/m$^2$ and yet more preferably between 15-20 g/m$^2$. The basis weight of the elastic layer may be between 10-140 g/m$^2$, preferably between 20-120 g/m$^2$ and more preferably between 25 and 100 g/m$^2$. These basis weights have proven useful in terms of fabric touch, elastic properties and stability.

Again going back to the more general context, the embossing projections are preferably heated to a temperature of greater 50° C., preferably to a temperature greater 80° ° C. for melting together the fibers of the precursor sheets under local pressure. Usually, preferred temperatures are even higher than 80° C. The exact choice of temperature depends on the kind of polymer material used. In this context, the temperature of the embossing projections may at least match the glass transition temperature of the polymers used, and may preferably be at least 10° C. or at least 20° C. above the glass transition temperature of the polymers used. The heating of the projections can be achieved by heating the entire surface of the activation roller(s) or by only locally heating the area around the embossing projections or the embossing projections themselves. An alternative embodiment uses ultrasonic embossing, where the embossing projections are vibrated at ultrasonic frequency to for melting together the fibers of the structures of the precursor sheet. This alternative is especially suitable if the difference in melting points of the materials of the carrier structure(s) on the one hand and the elastic structure on the other hand is relatively large. A localized impact can be realized by associating individual ultrasonic stacks with each embossing projection, for example. Temperature and ultrasonic vibration can also be used in combination.

A coating of the surfaces of the activation rollers around the embossing projections by inert materials like fluoropolymers, for example PTFE, can in some instances increase the accuracy and regularity of the embossing process, especially if thermal embossing is used.

Again referring specifically to the above-described embodiment of an elastically stretchable nonwoven sheet comprising elastic layers and carrier layers, in one embodiment, the elastic layer precursor structure is a structure formed from endless fibers comprising a thermoplastic elastomer material, preferably spunbonded fibers. As an alternative to spunbonding, in an alternative embodiment, melt blowing could be employed for forming the endless fibers of the elastic layer precursor structure. Correspondingly, in the product sheet, the elastic nonwoven structure in one embodiment is a spunbonded or meltblown structure comprising spunbonded or meltblown elastic endless fibers formed from a thermoplastic elastomer polymer material.

The thermoplastic elastomer material can comprise a thermoplastic polyolefin elastomer (TPE-o), preferably a thermoplastic polyolefin elastomer comprising propylene-α-olefin copolymers. Alternatively or additionally, meaning as a mixture, other thermoplastic elastomer materials like especially thermoplastic polyurethanes (TPU) or styrenic block copolymers (TPE-s) may be used. In one embodiment, up to 20 wt.-% and preferably up to 10 wt.-% of a thermoplastic olefin, such as a homo-polypropylene may be contained in the thermoplastic elastomer material next to the thermoplastic elastomer.

In one embodiment, a bicomponent elastic fiber can be formed from two different thermoplastic elastomers, arranged, for example, in a side-by-side or sheath-core configuration.

The first and, optionally, further the second carrier layer precursor structure is a spunbonded structure. Alternatively, also meltblown fiber structures or staple fiber structures such as carded structures can be used as carrier layer precursors.

In one embodiment, two carrier layer precursor structures on different sides of the elastic layer precursor structure are of different nature. For example, one of the carrier layer precursor structures is formed from spunbonded fibers and the other carrier layer precursor structure is formed from different spunbonded fibers or from meltblown or carded fibers. Correspondingly, in the product sheet, two nonwoven carrier layers on different sides of the elastic nonwoven layer are of different nature. For example, one of the nonwoven carrier layers may be a spunbonded nonwoven and the other nonwoven carrier layer may be a different spunbonded nonwoven or a meltblown or carded nonwoven.

In a baby diaper or adult incontinence product, it can be desired that the inner surface of the product has a certain elasticity and stickiness to skin to inhibit displacement of the worn product, while the outer surface should have as little stickiness as possible to fabrics of clothes. In this case, it may be preferred to have a spunbonded carrier nonwoven/precursor structure on one side of the elastic nonwoven/precursor structure, and a meltblown carrier nonwoven/precursor structure on the other side of the elastic nonwoven/precursor structure. Meltblown nonwovens generally show a bit more affinity to skin and other materials than spunbonded nonwovens, such that a requirement as just described may well be met with such a configuration.

Endless fibers are also sometimes called filaments in the art, but herein we will stick to the term fiber for both endless fibers, as produced by spunbonding, for example, and staple fibers of distinct length, that can be in the magnitude of one or a few centimeters.

In one embodiment, all precursor structures are spunbonded structures and all layers of the product sheet are spunbonded nonwoven fabrics.

As far as the fibers of the carrier precursor structures/layers are spunbonded fibers, these fibers can be crimped multicomponent fibers. In contrast to the technology disclosed in WO 2020/187540 A1, however, crimped fibers are not necessary to obtain a certain ability to stretch. In the context of the present invention, crimped fibers can also be useful, however, for example to increase loft and softness of the product.

In preferred embodiments, however, at least one of the carrier layers is formed from uncrimped monocomponent fibers. This is because softness and loft is in any case imparted by the activation, because the carrier layers made from uncrimped monocomponent fibers can be more stable, and because uncrimped monocomponent fibers are more cost efficient and easier to produce.

Generally, the fibers of the carrier precursor structures/layers are preferably formed from a thermoplastic polymer material, in particular from a polyolefin like polypropylene (PP), polyethylene (PE) or polypropylene-ethylene copolymers (co-PP).

Returning again to the more general context, multiple layers of precursor sheets can all be formed in-line, for example by spinning multiple structures in line onto a common conveyor belt. In an alternative embodiment, the sheets can be prefabricated materials and provided, for example, by unrolling from a roll fabricated in a different line or even site.

The precursor sheet provided in step (a) may in one embodiment be pre-compacted by passing it between a pair of pre-compaction rollers having flat surfaces before the combined bonding and activating of step (b).

The bond area in the pre-stretched sheet can in one embodiment lie between 2% and 15%, preferably between 4% and about 8% (referring to the bonding points imparted in step (b) of combined activation and bonding). The number of bonding points can be between 2 and 15, preferably between 4 and 8 (referring, again, to the bonding points imparted in step (b) of combined activation and bonding). In case the product sheet retracts from the pre-stretched state to a relaxed state afterwards, these bond areas and numbers of bonding points per unit area are proportionally increased. In such case, in the product sheet, the corresponding bond area in the product sheet can in one embodiment lie between 5% and 25%, preferably between 10% and about 20%. The number of corresponding bonding points can be between 5 and 25, preferably between 10 and 20.

Sheets produced according to the invention may be used in the manufacture of hygiene articles. For example, the sheets can be used for the manufacture of a taped diaper comprising the sheet as an elastic back ear material. Typical production processes currently employed in the industry in that application would require the material to be able to elastically stretch in CD. In another example, the sheets can be used for the manufacture of a diaper pant comprising the sheet as an elastic waist material. Typical production processes currently employed in the industry in that application would require the material to be able to elastically stretch in MD.

Figure 2:
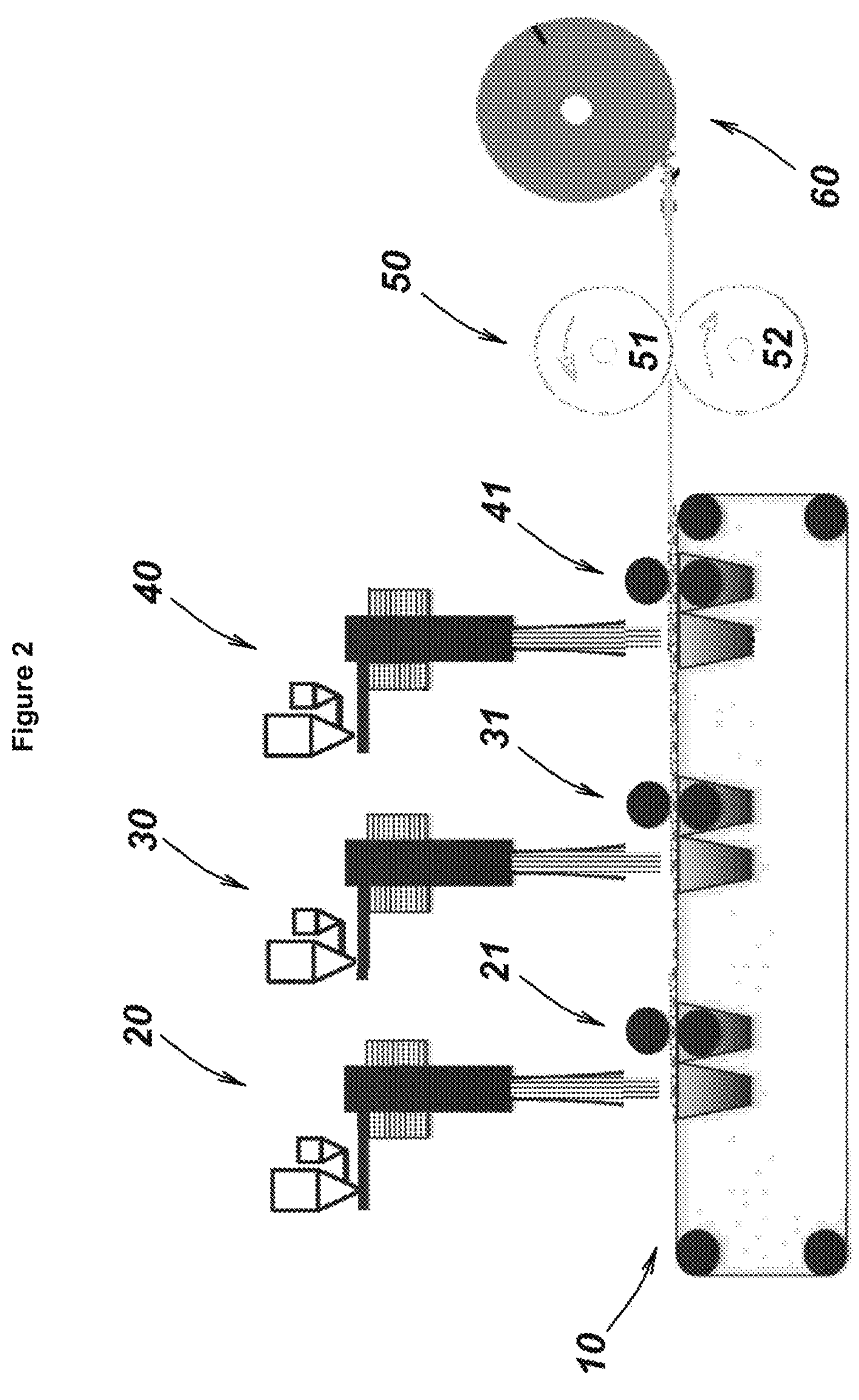
Figure 3:
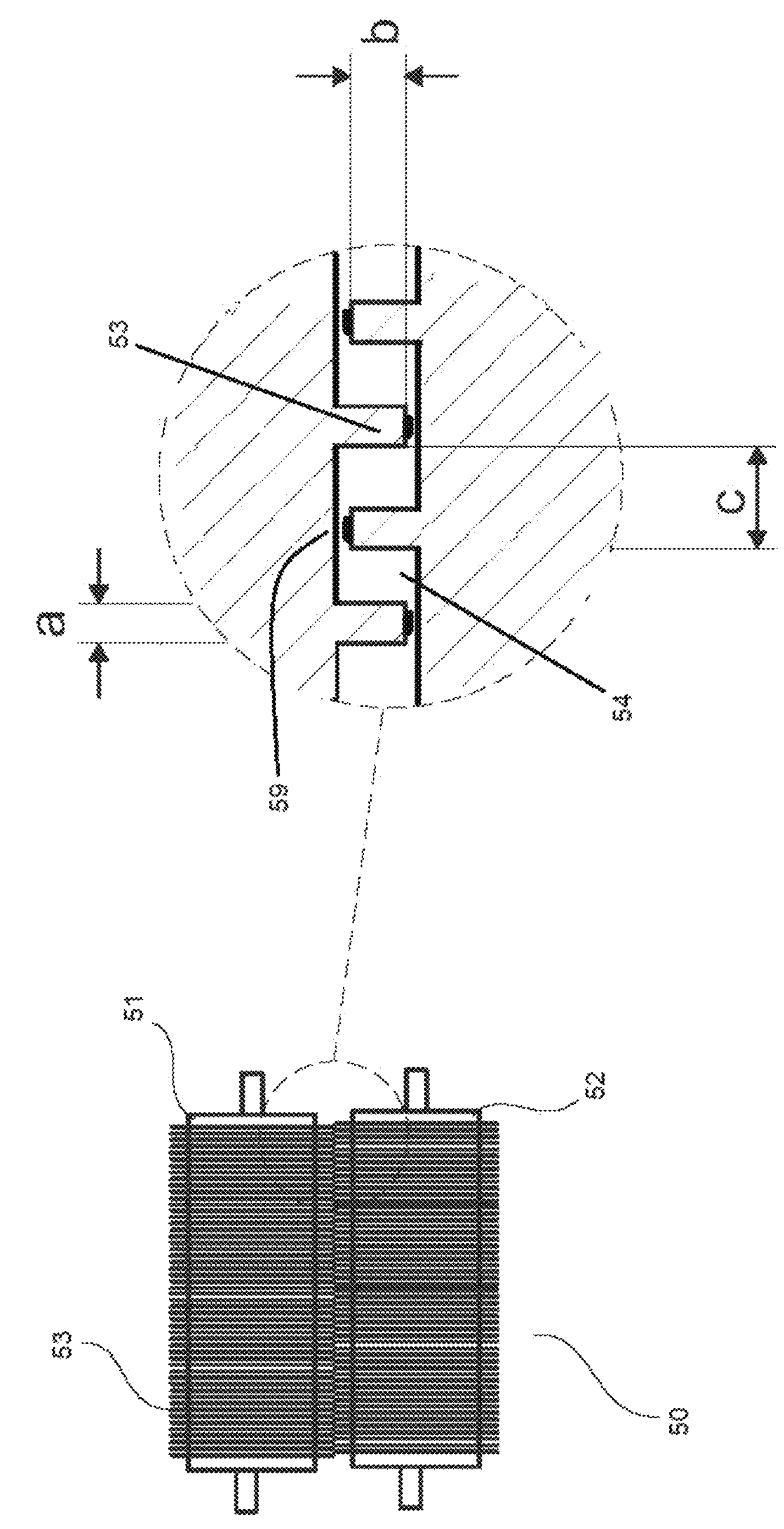
Figure 4:
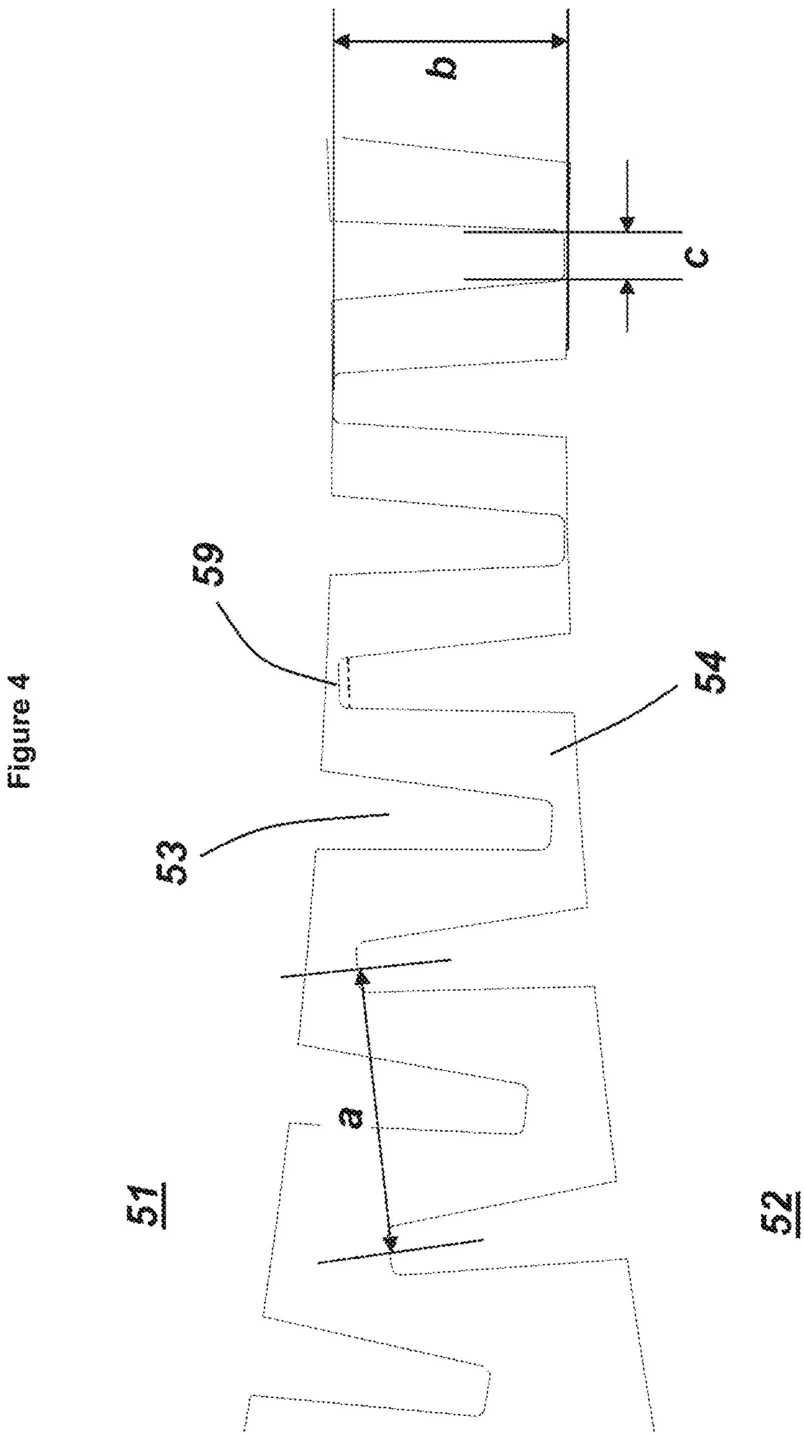
Figure 5:
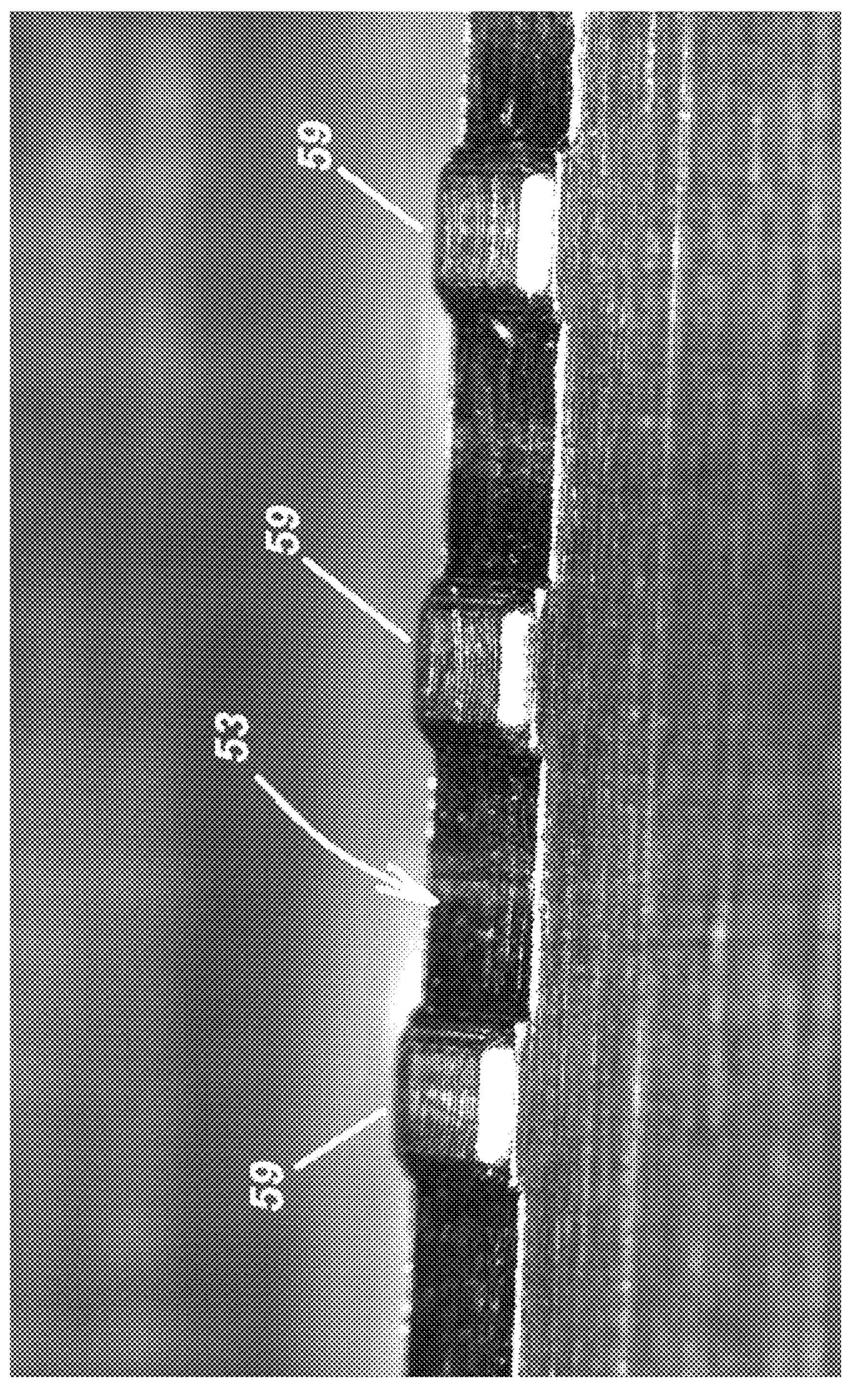
Figure 6:
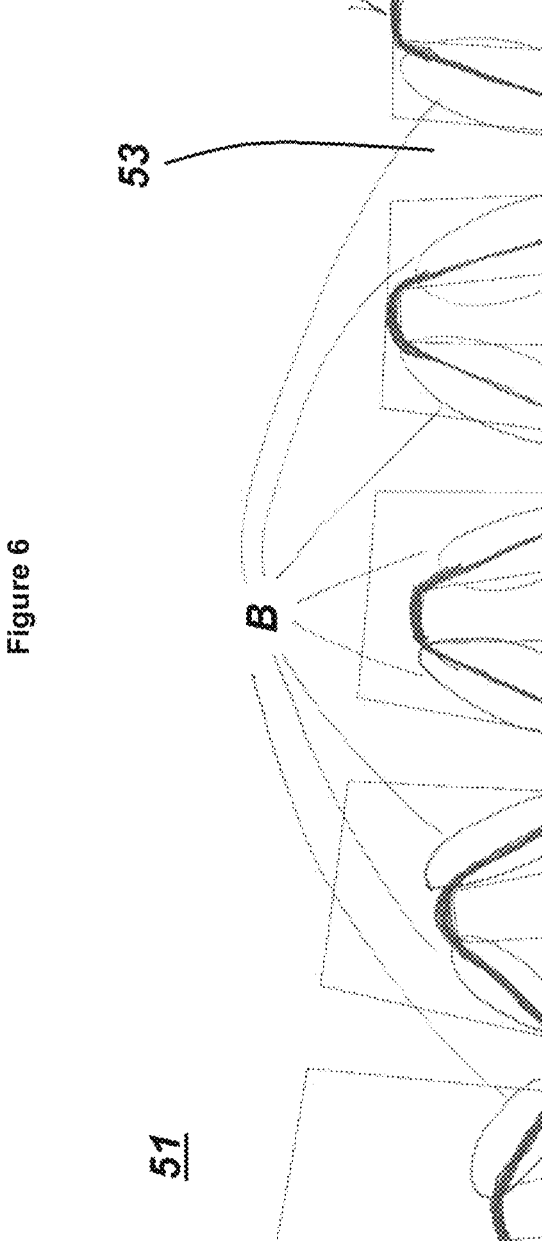

Further details and advantages of the invention will become apparent from the figures and examples described in the following. The figures show:

FIG. 1: a schematic cross-section of an elastically stretchable nonwoven sheet according to the invention;

FIG. 2: an exemplary machine setup for carrying out a method of the invention;

FIG. 3: an schematic illustration of a unit for concurrently activating, by stretch in cross-machine direction, and bonding the precursor sheet;

FIG. 4: an schematic illustration of a unit for concurrently activating, by stretch in machine direction, and bonding the precursor sheet;

FIG. 5: a picture of a crest line of a rib of an activation roller as schematically illustrated in FIG. 4, the rib having embossing projections on its crest line; and FIG. 6: a schematic illustration of a unit of FIG. 4 in operation.

FIG. 1 shows a schematic cross-section of an elastically stretchable nonwoven sheet 100 according to the invention, where an elastic nonwoven layer comprising elastic fibers 130 is sandwiched between first and second nonwoven carrier layers 120.

An exemplary machine setup for making an elastically stretchable nonwoven sheet 100 according to the invention is shown in FIG. 2.

The setup comprises a conveyor belt 10 and altogether three spunbonding machines 20, 30 and 40 arranged in line on the conveyor belt.

In each of the spunbonding machines, a molten thermoplastic polymer is extruded through the holes of a die. The extruded fiber strands are then quenched and drawn/stretched to form endless fibers, which are then laid onto the conveyor belt 10 or a web that has been previously deposited thereon.

The first spunbonding machine 20 deposits a first carrier precursor web of regular polypropylene endless fibers on the conveyor belt 10. The middle spunbonding machine 30 deposits an elastic carrier precursor web of endless fibers formed from a thermoplastic elastomer on the first carrier precursor web. The last spunbonding machine 40 deposits a second carrier precursor web of again regular polypropylene endless fibers on the elastic carrier precursor web.

Each of the spunbonding machines 20, 30 and 40 is followed by a pair of precompaction rollers 21, 31 and 41, respectively, for precompacting the respective webs.

The key feature of the inventive process is the unit 50 for concurrently activating and bonding the three-layered precursor sheet previously formed in the spunbonding machines. This unit comprises a pair of counter-rotating activation rollers 51, 52 having a plurality of meshing ribs and grooves arranged in parallel on their collaborating surfaces, with embossing projections being arranged along the crests of the ribs. The unit 50 will be described below in more detail.

At the end of the overall in-line process, the product sheet is collected on the product roll 60.

FIG. 3 shows an embodiment of activation rollers 51, 52 of a unit 50 that is configured for stretching the precursor sheet formed in the spunbonding machines 20, 30 and 40 in cross-machine direction. The right-hand side picture is an enlarged cross-section along an axial plane.

Both rollers 51 and 52 comprise a plurality of regularly spaced annular ribs 53 on their acting surfaces, between which grooves 54 are formed. The width of the ribs 53 is designated with letter "a", the depth of engagement is labelled with letter "b" and the distance between adjacent ribs is labelled with letter "c". The cross-machine directional stretch during activation is controlled by these three parameters. In an exemplary embodiment, the distance "c"

between adjacent ribs 53 can be about 6 mm. The depth of engagement "b" can be about 5 mm. The width "a" of the ribs 53 can be about 1 mm.

Another embodiment of activation rollers 51, 52 is discussed with reference to FIG. 4. The embodiment of FIG. 4 is configured for stretching the precursor sheet formed in the spunbonding machines 20, 30 and 40 in machine direction. The picture of FIG. 4 is an enlarged cross-section along a radial plane perpendicular to the roller axis.

Also in this embodiment, both rollers 51 and 52 comprise a plurality of regularly spaced ribs 53 on their acting surfaces, between which grooves 54 are formed. In contrast to the embodiment of FIG. 3, however, the ribs 53 in this embodiment are oriented in cross-machine direction and extend axially over the surfaces of the rollers 51 and 52.

Also in this embodiment, the width "a" of the ribs 53, the depth of engagement "b" and the distance between adjacent ribs 53 "c" controls the extent of the, in this case, machine directional stretch during activation. Also in this case, in an exemplary embodiment, the distance "c" between adjacent ribs 53 can be about 6 mm, the depth of engagement "b" can be about 5 mm, and the width "a" of the ribs 53 can be about 1 mm.

In both the embodiments of FIGS. 3 and 4, at the crest lines of each rib 53 on both rollers 51, 52 there is a series of embossing projections 59 for bonding the precursor web while it is stretched, or in other words for bonding the fabric simultaneously with the stretch activation.

FIG. 5 shows a picture of a crest line of a rib 53 of an activation roller 51, 52 as schematically illustrated in FIG. 4, the rib 53 having embossing projections 59 on its crest line.

The embossing projections 59 can have a height of about 0.2 to 0.5 mm, preferably about 0.3 mm on the crest line of the ribs 53. They can be approximately square-shaped, as shown in FIG. 5, or alternatively also, circular, oval rectangular, diamond shaped, etc. The bond area can be approximately 1 $mm^2$, so, for example, the square-shaped embossing projections 59 shown in FIG. 5 can be 1 mm by 1 mm. The distance between the bonding points can be approximately between 1-5 mm, preferably between 2-4 mm, and more preferably between 2.5-3 mm.

The resulting bond area in the pre-stretched web, considering the dimensions above, is preferably between about 4% and about 8%, distributed between 4-8 bonding points per $cm^2$. These bond areas and numbers of bonding points per unit area are proportionally increased after the product sheet retracts from a pre-stretched state in a relaxed state. Each of the two rollers 51, 52 provides half of the bonding points by the embossing projections 59 mounted thereon.

FIG. 6 shows a unit as shown in FIG. 4 in operation. From left to right in FIG. 6, the unbonded and unactivated precursor sheet consisting of the two carrier precursor webs and the elastic layer precursor web sandwiched there between enters the combined activation and bonding process. As the precursor sheet enters the nip of the two rollers 51, 52 the activation process is be initiated with the meshing ribs 53. In an exemplary embodiment, the distance from one crest line of one rib 53 sitting on a first roller 51 to a crest line of the closest rib 53 sitting on the other roller 52 can be approximately 2 mm as the precursor sheet enters the activation process. Due to the progressing engagement of the ribs 53 in the grooves 54 this distance is steadily increases, in an exemplary embodiment to a distance of approximately 5.2 mm in the center position where the ribs 53 and grooves 54 are fully engaged. The elastic layer precursor web during this process will elongate due to its elastic capability. The essentially inelastic fibers in the carrier precursor webs on each side of the elastic precursor webs, on the other hand, will re-orient themselves, creating high-density zones A around the crest lines of each rib 53, and low-density zones B there between.

At the maximum engagement point in the center position of the two rollers 51, 52, the embossing projections 59 on a rib 53 of one roller (here: the roller 51) will be in contact with the bottom of the opposite groove 54 of the opposite roller (here: the roller 52) and form a series of bonding points along the crest line of the rib 53, i.e. along a stripe-shaped high-density zone A of the pre-stretched precursor sheet.

As the material pre-stretched and bonded as described again exits the unit 50, the elastic fibers in the elastic nonwoven layer 120 of the product sheet 100 contract and revert the stretch of the material, such that it goes back to its original length in machine direction. The sections of the fibers in the carrier layers 110 and 130 that are not attached in a bonding point, during this relaxation process, re-orient and/or crimp, but always maintain the ability to again stretch in machine direction to the extent they have been pre-stretched in unit 50.

The dimensions of the ribs 53 and grooves 54, specifically the parameters "a", "b" and "c" can be varied as needed depending on the elongation property required in the product sheet. The values for these parameters exemplified in the description of FIGS. 4-6 result in a machine-directional pre-stretch by approximately 160% (from 2.0 mm to about 5.2 mm). As most hygiene product manufacturers presently require the ability to elastically stretch by approximately 100-150%, this design with a stretch property of 160% is suitable to match the demands in most cases.

The invention claimed is:

1. A method for manufacturing a nonwoven sheet, comprising:

(a) providing a precursor sheet; and (b) concurrently activating and bonding the precursor sheet to obtain the nonwoven sheet, wherein the activating comprises passing the precursor sheet between a pair of activation rollers having a plurality of meshing ribs and grooves arranged in parallel on their collaborating surfaces, thereby stretching the precursor sheet in a direction perpendicular to the orientation of the ribs and grooves, and wherein the bonding comprises an embossing of bonding points into the precursor sheet while it is stretched, the embossing being effected by embossing projections that are arranged along crests of the ribs and/or grooves on the activation roller surfaces.

2. The method of claim 1, wherein the method is a method for manufacturing an elastically stretchable nonwoven sheet, the sheet comprising a first nonwoven carrier layer, an elastic nonwoven layer comprising elastic fibers, and, optionally, a second nonwoven carrier layer, wherein the precursor sheet provided in step (a) comprises:

a first carrier structure, which is a precursor of the first nonwoven carrier layer of the sheet to be formed, an elastic structure comprising elastic fibers, which is a precursor of the elastic nonwoven layer of the sheet to be formed, and, optionally, a second carrier structure, which is a precursor of the optional second nonwoven carrier layer of the sheet to be formed.

3. The method of claim 2, wherein the first carrier structure is an unbonded fibrous carrier web, wherein the elastic structure is an unbonded elastic layer precursor web comprising elastic fibers, and wherein the optional second carrier structure is a second unbonded fibrous carrier web, wherein all fibrous webs are not bonded by calender embossing.

4. The method of claim 2, wherein the first carrier structure is a bonded nonwoven carrier layer, wherein the elastic structure is a bonded nonwoven layer comprising elastic fibers, and wherein the optional second carrier structure is a bonded nonwoven carrier layer, wherein all nonwoven layers are bonded by calender embossing.

5. The method of claim 1, wherein the ribs and grooves are oriented in machine direction and extend annularly over the surfaces of the rollers, such that the precursor sheet is stretched in cross-machine direction.

6. The method of claim 1, wherein the ribs and grooves are oriented in cross-machine direction and extend axially over the surfaces of the rollers, such that the precursor sheet is stretched in machine direction.

7. The method of claim 1, wherein in step (b) the precursor sheet is stretched to 150% of its original dimension in the direction perpendicular to the orientation of the ribs and grooves.

8. The method of claim 1, wherein the embossing projections are heated and/or vibrated at ultrasonic frequency for melting together fibers of structures of the precursor sheet under local pressure.

9. The method of claim 1, wherein the surface of one or both of the activation rollers is coated by an inert material around the embossing projections, wherein the inert material is a fluoropolymer.

10. The method of claim 1, wherein in step (b) the precursor sheet is stretched to 200% of its original dimension in the direction perpendicular to the orientation of the ribs and grooves.

11. The method of claim 1, wherein the surface of one or both of the activation rollers is coated by an inert material around the embossing projections, wherein the inert material is PTFE.

* * * * *